US00PP27302P2

(12) United States Plant Patent
Wood

(10) Patent No.: US PP27,302 P2
(45) Date of Patent: Oct. 25, 2016

(54) ***HYDRANGEA* PLANT NAMED 'SMHPPINO'**

(50) Latin Name: *Hydrangea paniculata*
Varietal Denomination: SMHPPINO

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 14/544,635

(22) Filed: Jan. 23, 2015

(51) Int. Cl.
*A01H 5/00* (2006.01)

(52) U.S. Cl.
USPC ..... Plt./250

(58) Field of Classification Search
USPC ..... Plt./226, 250
See application file for complete search history.

(56) References Cited

PUBLICATIONS

PLUTO: Plant Variety Database, Jan. 20, 2016, citation for 'SMHPPINO'. 1 page.*

* cited by examiner

*Primary Examiner* — Susan McCormick Ewoldt
*Assistant Examiner* — Karen Redden
(74) *Attorney, Agent, or Firm* — C. A Whealy

(57) ABSTRACT

A new and distinct cultivar of *Hydrangea* plant named 'SMHPPINO', characterized by its upright and somewhat outwardly spreading plant habit; strong and sturdy stems; freely flowering habit; broad showy inflorescences with sterile flowers that are light green in color; and good garden performance.

2 Drawing Sheets

Botanical designation: *Hydrangea paniculata.*
Cultivar denomination: 'SMHPPINO'.

BACKGROUND OF THE INVENTION

The present invention relates to a new and distinct *Hydrangea* plant, botanically known as *Hydrangea paniculata* and hereinafter referred to by the name 'SMHPPINO'.

The new *Hydrangea* plant is a product of a planned breeding program conducted by the Inventor in Grand Haven, Mich. The objective of the breeding program was to develop new *Hydrangea* plants with strong stems and large and attractive inflorescences.

The new *Hydrangea* plant originated from an open-pollination in July, 2007 of *Hydrangea paniculata* 'BarF2', not patented, as the female, or seed parent and an unknown selection of *Hydrangea paniculata* as the male, or pollen, parent. The new *Hydrangea* plant was discovered and selected by the Inventor as a single flowering plant from within the progeny of the stated open-pollination in a controlled environment in Grand Haven, Mich. in July, 2009.

Asexual reproduction of the new *Hydrangea* plant by softwood cuttings in a controlled environment in Grand Haven, Mich. since July, 2009 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMHPPINO'. These characteristics in combination distinguish 'SMHPPINO' as a new and distinct *Hydrangea* plant:

1. Upright and somewhat outwardly spreading plant habit.
2. Strong and sturdy stems.
3. Freely flowering habit.
4. Broad showy inflorescences with sterile flowers that are light green in color.
5. Good garden performance.

Plants of the new *Hydrangea* differ from plants of the female parent, 'BarF2', in the following characteristics:

1. Plants of the new *Hydrangea* have stronger stems than plants of 'BarF2'.
2. Plants of the new *Hydrangea* have broader and denser inflorescences than plants of 'BarF2'.
3. Plants of the new *Hydrangea* and 'BarF2' differ in flower color as plants of 'BarF2' have white-colored sterile flowers.

Plants of the new *Hydrangea* can be compared to plants of *Hydrangea paniculata* 'Limelight', disclosed in U.S. Plant Pat. No. 12,874. In side-by-side comparisons, plants of the new *Hydrangea* differed primarily from plants of 'Limelight' in the following characteristics:

1. Plants of the new *Hydrangea* were more compact than plants of 'Limelight'.
2. Plants of the new *Hydrangea* had broader and denser inflorescences than plants of 'Limelight'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SMHPPINO' growing in an outdoor nursery.

The photograph on the second sheet is a close-up view of a typical flowering plant of 'SMHPPINO'.

Plants used in the photographs were three years old.

DETAILED BOTANICAL DESCRIPTION

Plants used for the following description were grown during the summer in three-gallon containers in a polypropylene-covered shadehouse in Grand Haven, Mich. and under cultural practices typical of commercial *Hydrangea* production. During the production of the plants, day temperatures ranged from 18° C. to 27° C. and night temperatures ranged from 5° C. to 10° C. Plants of the new *Hydrangea* were two years old when the photographs and description were taken. Plants were overwintered in a polyethylene-covered greenhouse. In the following description, color references are made to The Royal Horticultural Society Colour Chart, 1995 Edition, except where general terms of ordinary dictionary significance are used.

Botanical description: *Hydrangea paniculata* 'SMHPPINO'.

Parentage:

- *Female, or seed, parent.*—*Hydrangea paniculata* 'BarF2', not patented.
- *Male, or pollen, parent.*—Unknown selection of *Hydrangea paniculata*, not patented.

Propagation:

- *Type cutting.*—By softwood cuttings.
- *Time to initiate roots, summer.*—About 18 days at temperatures about 27° C.
- *Time to produce a rooted young plant, summer.*—About two months at temperatures about 27° C.
- *Root description.*—Fine and thick; white and brown in color.
- *Rooting habit.*—Freely branching; dense.

Plant description:

- *Plant form and growth habit.*—Perennial deciduous shrub; upright and somewhat outwardly spreading plant habit; broad inverted triangle; strong and sturdy lateral branches; freely branching habit with about 29 lateral branches developing per plant; vigorous growth habit.
- *Plant height.*—About 93.5 cm.
- *Plant diameter or area of spread.*—About 138 cm.
- *Lateral branches.*—Length: About 80 cm. Diameter: About 1 cm. Internode length: About 3 cm to 7.9 cm. Texture: Pubescent. Strength: Strong, sturdy; rigid. Aspect: Erect to about 35° from vertical. Color, developing: Close to 194B overlain with close to 199A and blending into close to 200D. Color, developed: Close to 138B overlain with close to 199A.

Leaf description:

- *Arrangement.*—Opposite, simple.
- *Length.*—About 13.1 cm.
- *Width.*—About 6.9 cm.
- *Shape.*—Ovate.
- *Apex.*—Acuminate.
- *Base.*—Obtuse to cuneate.
- *Margin.*—Serrulate; slightly undulate.
- *Texture, upper and lower surfaces.*—Slightly pubescent; rugose.
- *Venation pattern.*—Pinnate.
- *Color.*—Developing leaves, upper surface: Close to 138A tinted with close to 145A. Developing leaves, lower surface: Close to 138B. Fully expanded leaves, upper surface: Close to 137A; venation, close to 145A. Fully expanded leaves, lower surface: Close to 138B; venation, close to 145C.
- *Petioles.*—Length: About 2.3 cm. Diameter: About 3 mm. Texture, upper surface: Smooth, glabrous. Texture, lower surface: Slightly pubescent. Color, upper surface: Close to 145A. Color, lower surface: Close to 145C.

Inflorescence & flower description:

- *Flower type and habit.*—Single sterile and fertile flowers arranged on large broad terminal panicles; flowers face upright and outwardly.
- *Fragrance.*—None detected.
- *Natural flowering season.*—Continuous flowering from mid-July until October in Grand Haven, Mich.
- *Quantity of flowers.*—Freely flowering habit; at least 100 fertile flowers and at least 1,000 sterile flowers develop per inflorescence.
- *Inflorescence height.*—About 28.3 cm.
- *Inflorescence diameter.*—About 20.5 cm.
- *Flower diameter, fertile flowers.*—About 3 mm.
- *Flower depth (height), fertile flowers.*—About 2 cm.
- *Flower diameter, sterile flowers.*—About 3.5 cm.
- *Flower depth (height), sterile flowers.*—About 2.75 mm.
- *Flower buds, fertile flowers.*—Length: About 3 mm. Diameter: About 2.5 mm. Shape: Orbicular, lobed. Color: Close to 145C.
- *Flower buds, sterile flowers.*—Length: About 1.2 mm. Diameter: About 1.2 mm. Shape: Orbicular, lobed. Color: Close to 155A.
- *Petals, fertile flowers.*—Arrangement: Four in a single whorl. Length: About 1 mm. Width: About 1.25 mm. Shape: Ovate. Apex: Acute. Base: Obtuse. Margin: Entire. Texture, upper and lower surfaces: Smooth, glabrous. Color: When opening, upper and lower surfaces: Close to 145A. Fully opened, upper surface: Close to 145A; becoming closer to 145B with development. Fully opened, lower surface: Close to 145B; becoming closer to 145C with development.
- *Petals, sterile flowers.*—Arrangement: Four in a single whorl. Length: About 1 mm. Width: About 1.25 mm. Shape: Elliptic to ovate. Apex: Acute. Base: Rounded to slightly acute. Margin: Entire. Texture, upper and lower surfaces: Smooth, glabrous. Color: When opening, upper surface: Close to 147C. When opening, lower surface: Close to 147D. Fully opened, upper and lower surfaces: Close to 155A; color does not change with development.
- *Sepals, fertile flowers.*—Quantity per flower: Five in a single whorl. Length: About 1 mm. Width: About 2 mm. Shape: Fused. Apex: Acute. Base: Obtuse. Margin: Entire. Texture, upper and lower surfaces: Smooth, glabrous. Color: When opening and fully opened, upper surface: Close to 145A; color does not change with development. When opening and fully opened, lower surface: Close to 145C; color does not change with development.

*Sepals, sterile flowers*.—Quantity per flower: Four in a single whorl. Length: About 1.6 cm. Width: About 1.6 cm. Shape: Elliptical to obovate. Apex: Obtuse. Base: Obtuse to slightly acute. Margin: Entire. Texture, upper and lower surfaces: Smooth, glabrous. Color: When opening, upper and lower surfaces: Close to 155A; striations, close to 145C. Fully opened, upper and lower surfaces: Close to 155A; color becoming closer to 186A with development.

*Pedicels, fertile flowers*.—Length: About 1 mm. Diameter: About 1 mm. Angle: Erect to about 90° from inflorescence axis. Strength: Strong, sturdy. Texture: Slightly pubescent. Color: Close to 145D.

*Pedicels, sterile flowers*.—Length: About 2.2 cm. Diameter: About 1.2 mm. Angle: Erect to about 45° from inflorescence axis. Strength: Strong, sturdy. Texture: Smooth, glabrous. Color: Close to 155A.

*Reproductive organs, fertile flowers*.—Stamens: Quantity per flower: About eight. Filament length: About 0.75 mm. Filament color: Close to 145A. Anther shape: Lanceolate. Anther length: About 1 mm. Anther color: Close to 145A. Pollen amount: None observed. Pistils: Pistil quantity per flower: One. Pistil length: About 1 mm. Stigma shape: Club-shaped. Stigma color: Close to 145A. Style length: About 0.75 mm. Style color: Close to 145A. Ovary color: Close to 155A and 145B.

*Reproductive organs, sterile flowers*.—Stamens: Quantity per flower: About eight. Filament length: About 2.5 mm. Filament color: Close to 155C. Anther shape: Lobed. Anther length: About 1 mm. Anther color: Close to 162B. Pollen amount: Scarce. Pollen color: Close to 155B. Pistils: Pistil quantity per flower: One. Pistil length: About 1 mm. Stigma shape: Club-shaped. Stigma color: Close to 145A. Style length: About 0.75 mm. Style color: Close to 145A. Ovary color: Close to 155A and 145B.

*Seeds and fruits*.—Seed and fruit development has not been observed on plants of the new *Hydrangea*.

Disease & pest resistance: Plants of the new *Hydrangea* have not been observed to be resistant to pathogens and pests common to *Hydrangea* plants.

Garden performance: Plants of the new *Hydrangea* have been observed to have good garden performance by exhibiting good tolerance to rain and wind; to be resistant to sun scald; and to tolerate temperatures ranging from about −32° C. to about 36° C.

It is claimed:

1. A new and distinct *Hydrangea* plant named 'SMHP-PINO' as illustrated and described.

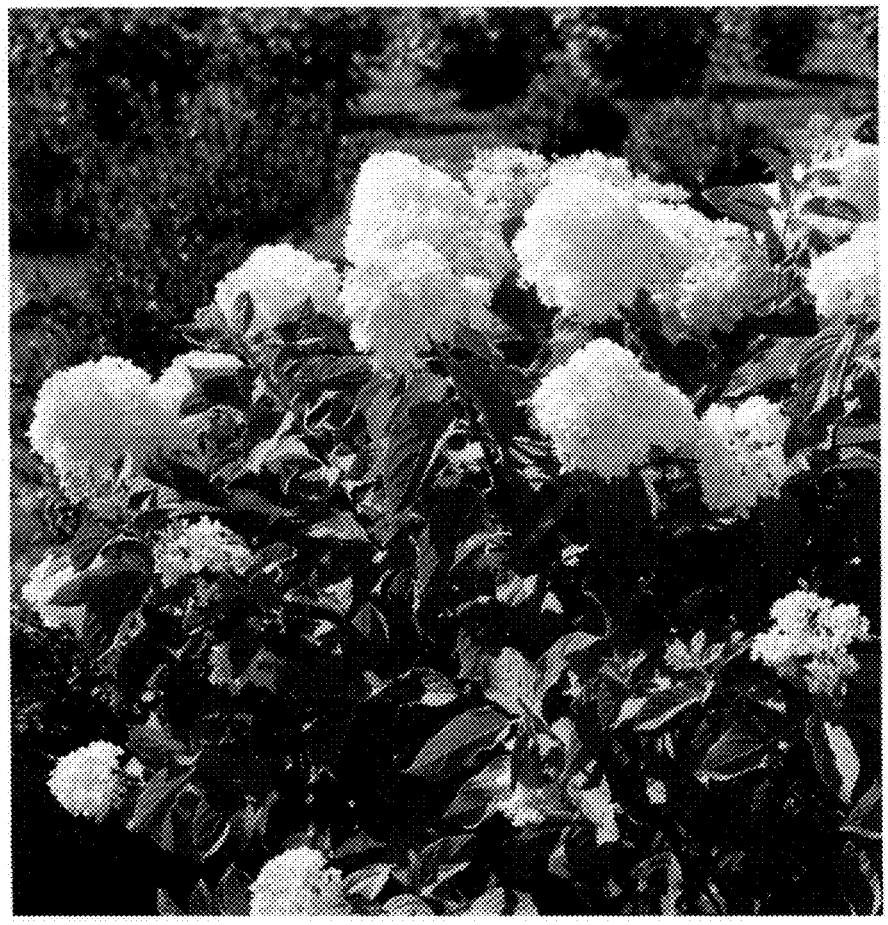

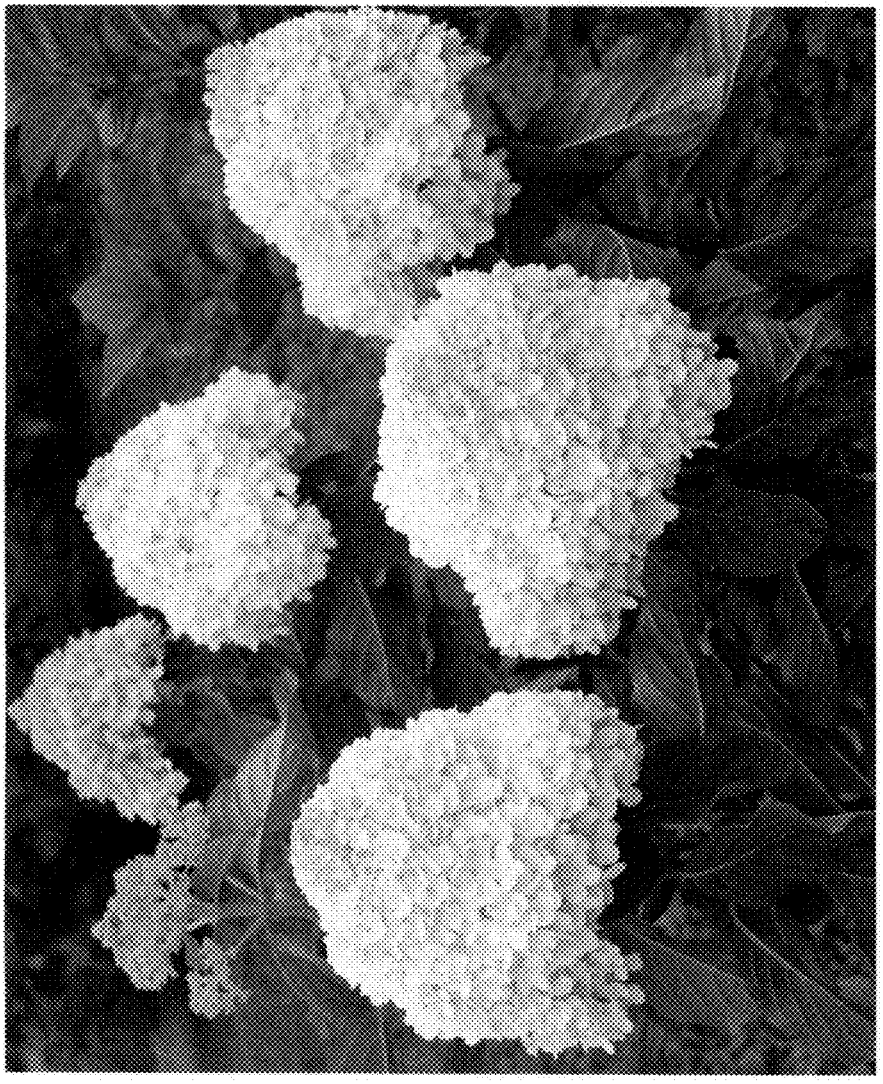

* * * * *